(12) United States Patent
Er et al.

(10) Patent No.: US 6,266,565 B1
(45) Date of Patent: Jul. 24, 2001

(54) METHOD AND APPARATUS FOR DETECTING AND DISPLAYING P-WAVE AND R-WAVE HISTOGRAMS FOR AN IMPLANT MEDICAL DEVICE

(75) Inventors: Siew Bee Er, Newhall; Laurence S. Sloman, West Hollywood, both of CA (US); James E. Tyler, Forsyth, GA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/454,647

(22) Filed: Dec. 6, 1999

(51) Int. Cl.$^7$ ........................................... A61N 1/37
(52) U.S. Cl. ............................... 607/27; 600/510
(58) Field of Search ..................... 607/27, 28, 29, 607/30, 31, 32; 600/510

(56) References Cited

U.S. PATENT DOCUMENTS

| | | | |
|---|---|---|---|
| 5,024,221 | 6/1991 | Morgan | 128/419 |
| 5,487,755 | 1/1996 | Snell et al. | 607/27 |
| 5,944,744 | 8/1999 | Paul et al. | 607/9 |

*Primary Examiner*—Scott M. Getzow

(57) ABSTRACT

A pacemaker, or other implantable medical device, connected to heart tissue, detects atrial and ventricular electrical signals. The pacemaker analyzes the signals to determine whether the signals are representative of P-waves or R-waves according to atrial and ventricular sensitivity threshold values. Signals determined to be P-waves or R-waves are identified as sensed signals. Otherwise the signals are identified as not-sensed signals. The pacemaker further determines whether the sensed signals were detected during a refractory period or an alert period and its current tracking mode (e.g., VDD, DDD vs. DDI, VVI). Information pertaining to these atrial and ventricular signals is transmitted to an external programmer which generates representative histograms. The histograms present the number of counts detected within each of a set of high pass filtered amplitude ranges and further indicate the relative numbers of sensed vs. not-sensed counts. For the sensed counts, the histogram may further indicate the relative numbers of counts detected during refractory periods and alert periods. The histograms additionally show the applicable atrial or ventricular sensitivity threshold values to visually assist a physician in determining whether the threshold values are set properly. An auto-sensitivity adjustment system is also provided to determine optimal sensitivity threshold values.

50 Claims, 8 Drawing Sheets

METHOD AND APPARATUS FOR DETECTING AND DISPLAYING P-WAVE AND R-WAVE HISTOGRAMS FOR AN IMPLANT MEDICAL DEVICE

FIELD OF THE INVENTION

The invention generally relates to implantable medical devices and to external programmers used in connection therewith and in particular to methods and apparatus for processing information with an external programmer pertaining to P-waves and R-waves detected by the implantable medical device.

BACKGROUND OF THE INVENTION

Implantable medical devices, particularly pacemakers, are often configured to be used in conjunction with an external programmer which allows a physician to control the implantable medical device and to display information sensed by the device. For example, with a pacemaker, the external programmer may operate to control the parameters by which the pacemaker paces the heart and to display intracardiac electrograms (IEGMs) and other useful diagnostic information.

One example of an external programmer for use with a pacemaker is an analyzer-programmer system (APS) identified as the APS II system which is provided by St. Jude Medical CRMD of Sylmar, Calif. Components of the APS II system operate to allow a physician to program the operation of the pacemaker to, for example, control the manner by which the pacemaker detects arrhythmia conditions within the heart and responds thereto. In particular, the APS II system allows the physician to specify atrial and ventricular sensitivity threshold values with which the pacemaker senses P-waves and R-waves within, respectively, the atrium and ventricle of the heart and to further specify the mode employed by the pacemaker for pacing the heart in circumstances where expected P-waves or R-waves are not-sensed. An exemplary single-chambered pacing mode is VVI wherein both pacing and sensing is performed in the ventricle and wherein, upon detection of an R-wave, subsequent pacing within the ventricle is inhibited for a predetermined pacing interval. An exemplary dual-chambered pacing mode is VDD wherein sensing is performed in both the atrium and the ventricle but pacing is performed only in the ventricle. With the VDD mode, which is also referred to as the P tracking mode, detection of an R-wave in the ventricle triggers a pacing pulse, then further pacing is inhibited for the duration of the pacing interval. U.S. Pat. No. 5,487,755, to Snell et al. entitled "Method for Displaying a Sequential Series of Pacing Events" provides a detailed description of the operation of the APS II system of St. Jude Medical CRMD (formerly Pacesetter, Inc.) including a description of various pacing modes. U.S. Pat. No. 5,487,755 is incorporated by reference herein.

It is particularly important that the atrial and ventricular sensitivity threshold values are set optimally to ensure that P-waves and R-waves are properly detected so that the correct pacing action is taken by the pacemaker based upon the selected pacing mode. If the sensitivity threshold values are set too low, then random noise spikes may be misinterpreted as P-waves or R-waves and incorrect action may be taken by the pacemaker, perhaps resulting in the failure to provide pacing pulses when otherwise required. If the sensitivity threshold values are set too high, then P-waves or R-waves that are actually present may go undetected and again incorrect action maybe taken by the pacemaker including, for example, providing a pacing pulse when none is needed, perhaps triggering pacemaker mediated tachycardia (PMT). Although the atrial and ventricular sensitivity threshold values are typically not the only factors employed to determine whether a sensed electrical signal is a P-wave or an R-wave, the sensitivity threshold values are key factors in that determination and optimal sensitivity threshold values are critical for the safe and reliable operation of the pacemaker.

Although the aforementioned APS II system provides much useful diagnostic information to assist a physician in setting or adjusting the atrial and ventricular sensitivity values, room for further improvement remains. In particular, it would be desirable to provide a diagnostic display which allows the physician to easily visually verify that the atrial and ventricular sensitivity threshold values are properly set and it is primarily to that end that the present invention is directed. Additionally, it would be desirable to provide a method whereby the sensitivity threshold values may be automatically adjusted to a more optimal value by the pacemaker itself and aspects of the present invention are directed to that end as well.

SUMMARY OF THE INVENTION

In accordance with the present invention, a method is provided for processing information pertaining to electrical heart signals, such as P-waves and R-waves, to generate histograms representative of the information. The method is employed using an implantable medical device and an external display device, e.g., an external programmer, wherein the implantable medical device is connected to heart tissue and is capable of sensing electrical activity within the heart tissue. The method includes the steps of detecting a plurality of signals representative of electrical depolarization activity within the heart tissue connected to the implantable medical device and determining, for each respective detected signal, whether the signal corresponds to a predetermined type of heart tissue depolarization. The method also includes the steps of transmitting from the implantable medical device to the external display device, for each respective detected signal, a signal representative of the degree of depolarization of the detected signal as well as a signal indicative of whether the detected signal is of the predetermined type of heart tissue depolarization. The method additionally includes the steps of receiving the transmitted signals at the external display device, processing the signals to generate a histogram representative of the plurality of detected signals as a function of the degree of depolarization of the signals and further representative of whether the signals were determined to correspond to the predetermined type of heart tissue depolarization, and graphically displaying the histogram.

In accordance with an exemplary embodiment, wherein the implantable medical device includes a pacemaker, the predetermined type of heart tissue depolarization sensed is either a P-wave depolarization or an R-wave depolarization and separate histograms are generated for the P-waves and the R-waves. Signals that are identified as P-waves or R-waves are shown in their respective histograms as sensed signals and signals that cannot be identified as corresponding to P-waves or R-waves (e.g., because they don't satisfy a sensitivity threshold value criteria) are shown in their respective histograms as not-sensed signals. Each sensed/not-sensed histogram also identifies portions of the sensed signals that were detected during either an alert period or a refractory period. Additionally, sensed/not-sensed histograms are preferably provided which correspond to the current tracking (e.g., VDD, DDD) or non-tracking (e.g., DDI, VVI) mode of operation.

Also in the exemplary embodiment, the step of determining whether each signal corresponds to either a P-wave or an R-wave is performed, in part, by filtering, e.g., high-pass filtering, each signal to obtain a filtered amplitude and then comparing the filtered amplitude of each signal with a predetermined sensitivity threshold, such as 0.75 mv (millivolts). The predetermined sensitivity threshold is displayed in the histogram. The predetermined sensitivity threshold may also be adjusted based upon a comparison of a ratio of the number of sensed and not-sensed signals received as discussed further below. Such an adjustment may be triggered upon detection of an automode switching event, i.e., when the onset of an atrial tachycardia within the heart tissue is detected the pacemaker may switch from a tracking (e.g., VDD, DDD) to a non-tracking (e.g., DDI, VVI) operational mode.

Hence, with the present invention, methods are provided for graphically displaying histograms representative of sensed and not-sensed P-waves and R-waves to thereby assist the physician in making quick and informed decisions regarding, for example, any needed adjustment in atrial and ventricular sensitivity threshold values. Such adjustments are made automatically by the pacemaker, e.g., upon detection of an automode switching event that switches between a tracking (e.g., VDD, DDD) or a non-tracking (DDI, VVI) mode of operation, by comparing ratios of sensed and not-sensed signals to automatically achieve more optimal threshold sensitivity values.

Other advantages of the invention are achieved as well. Apparatus embodiments of the invention are also provided.

DETAILED DESCRIPTION OF THE INVENTION

The present invention relates to improved techniques for providing information to a physician regarding P-waves and R-waves detected by an implantable medical device. The invention will be described primarily with reference to a pacemaker used in conjunction with an external programmer, but principles of the invention may be applicable to other implantable medical devices and other external devices as well.

The figures illustrate a pacemaker/programmer system having a pacemaker for implantation into a patient's body and an external programmer for programming the operation of the pacemaker and for processing and displaying information received from the pacemaker regarding the condition of a patient in which the pacemaker is implanted. The external programmer includes processing units for receiving information transmitted by the pacemaker and for generating a wide variety of graphical displays of the information under the control of the physician operating the external programmer. In the following descriptions, for the sake of clarity in describing pertinent features of the invention, many details of the operation of the overall pacemaker/programmer system are not provided herein. Such details may be found in the aforementioned U.S. Pat. No. 5,487,755 to Snell et al.

Figure 1:
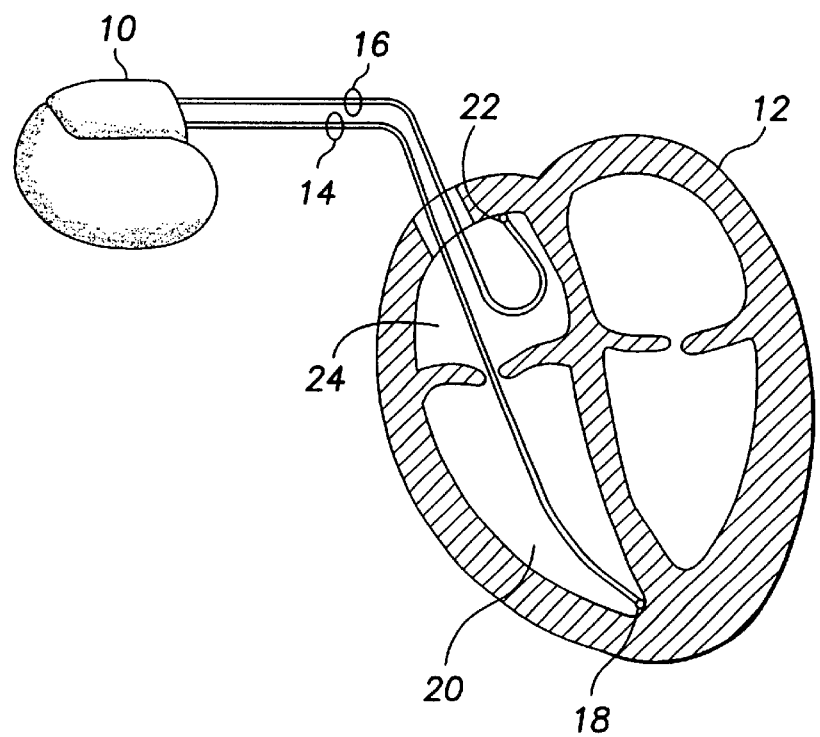
FIG. 1 shows an implantable pacemaker coupled to a heart via a pair of electrical leads.

FIG. 1 illustrates an implantable pacemaker 10 coupled to a patient's heart 12 by way of a ventricular lead 14 and an atrial lead 16. Ventricular lead 14 includes an electrode 18 positioned in the right ventricle 20 of the heart and atrial lead 16 includes an electrode 22 positioned in the right atrium 24 of the heart. Various internal components of the pacemaker operate to sense electrical depolarization activity of the heart, such as the presence of P-waves and R-waves, using electrodes 18 and 22 and to selectively stimulate the heart in response to the sensed electrical activity by conducting electrical stimulation pulses to the heart using the electrodes. Although not shown in FIG. 1, the pacemaker includes a transmitter for transmitting signals representative of the sensed electrical activity to an external programmer.

Figure 2:
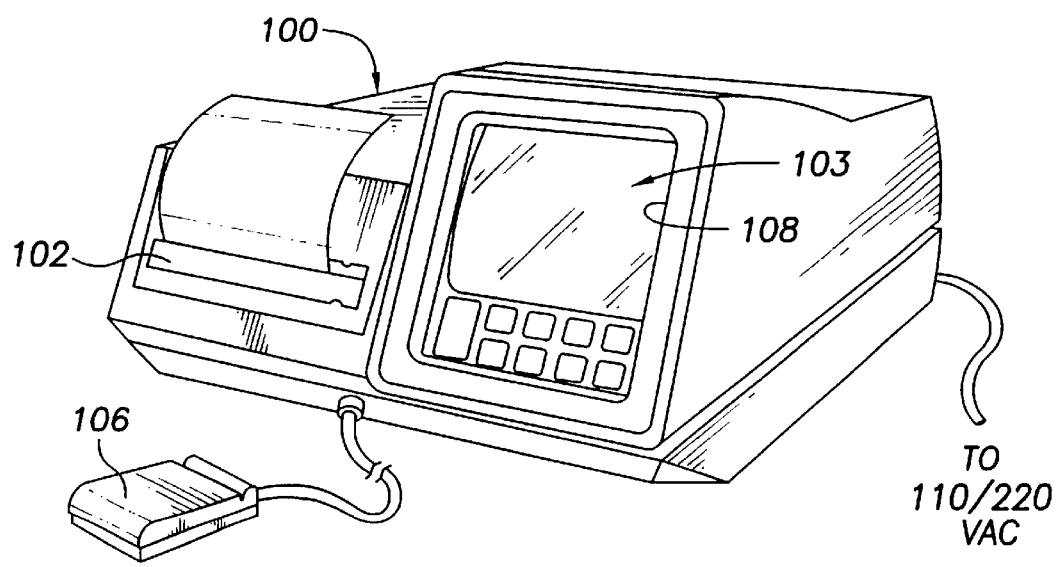
FIG. 2 is a perspective view of an external programmer that may be used for controlling the implantable pacemaker of FIG. 1.

FIG. 2 illustrates an external programmer 100 configured for receiving the aforementioned signals from pacemaker 10 (FIG. 1) and for generating graphical displays or printouts presenting histograms representative of the sensed electrical activity, including P-wave and R-wave histograms. Programmer 100 includes a printer 102 for printing out hard copies of the histograms and a display screen 103 for displaying the histograms. The operation of the pacemaker and the generation of the histograms, or other graphical displays, are subject to the control of a physician or other user operating the external programmer. To this end, external programmer 100 presents various menus on display screen 103 for use in controlling operation of the programmer to program pacemaker 10 (FIG. 1) to, for example, control the sensitivity with which P-wave and R-wave electrical activity is detected by the pacemaker or to control the manner by which the pacemaker responds to the detection of P-waves and R-waves. Various menus are also presented on display screen 103 for use in controlling operation of the programmer to generate displays on display screen 103 of information received from the pacemaker including the aforementioned histograms. Programmer 100 preferably receives menu selections from the physician through a touch screen 108 which overlays display screen 103. Actual programming of the pacemaker is achieved using a telemetry head 106 which, in use, is placed in proximity to the pacemaker 10.

Figure 3:
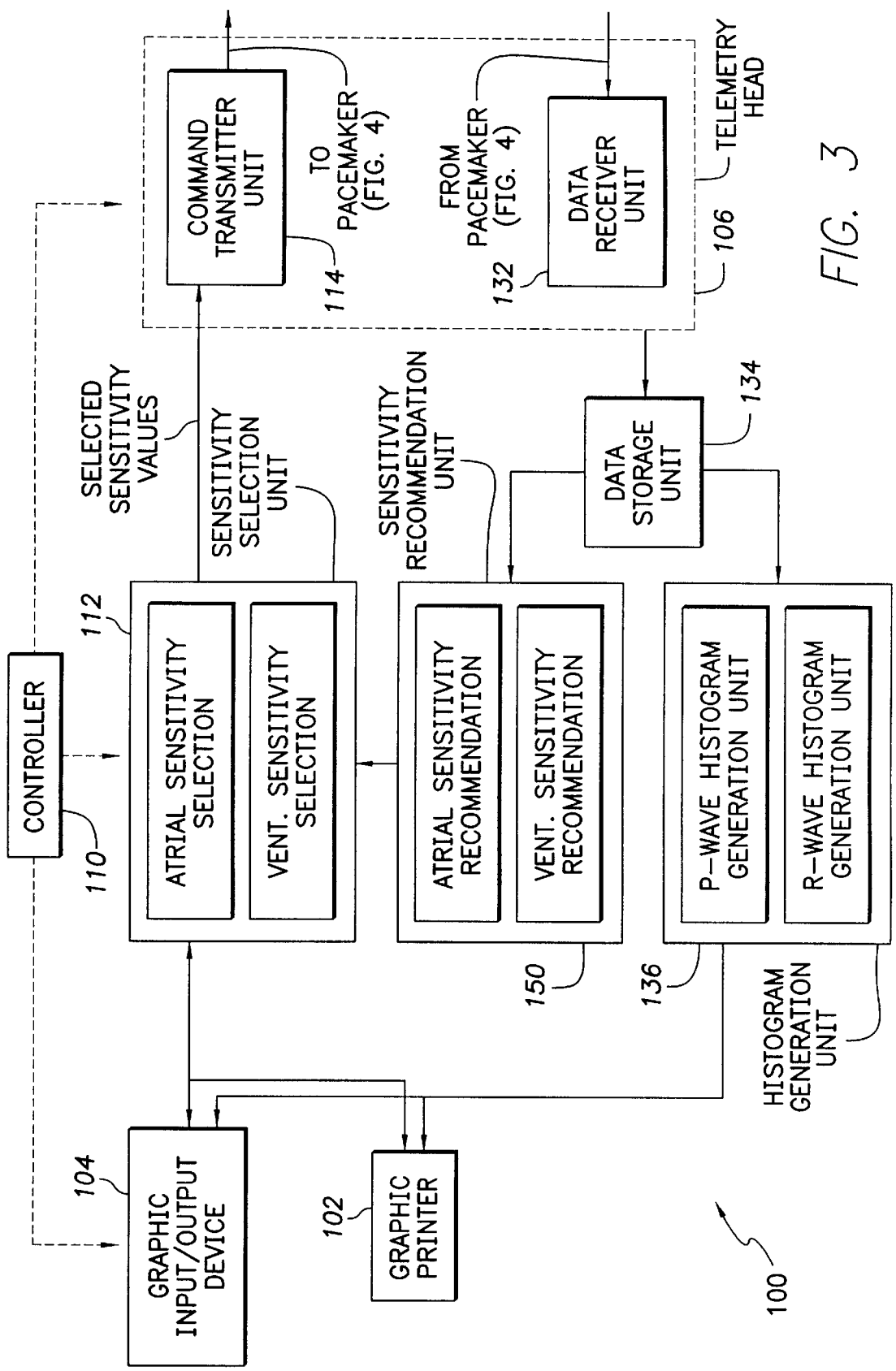
FIG. 3 is block diagram of pertinent components of an exemplary embodiment of the external programmer of FIG. 2 for use in generating and displaying histograms of P-waves and R-waves based upon data received from the implantable pacemaker of FIG. 1.
Figure 4:
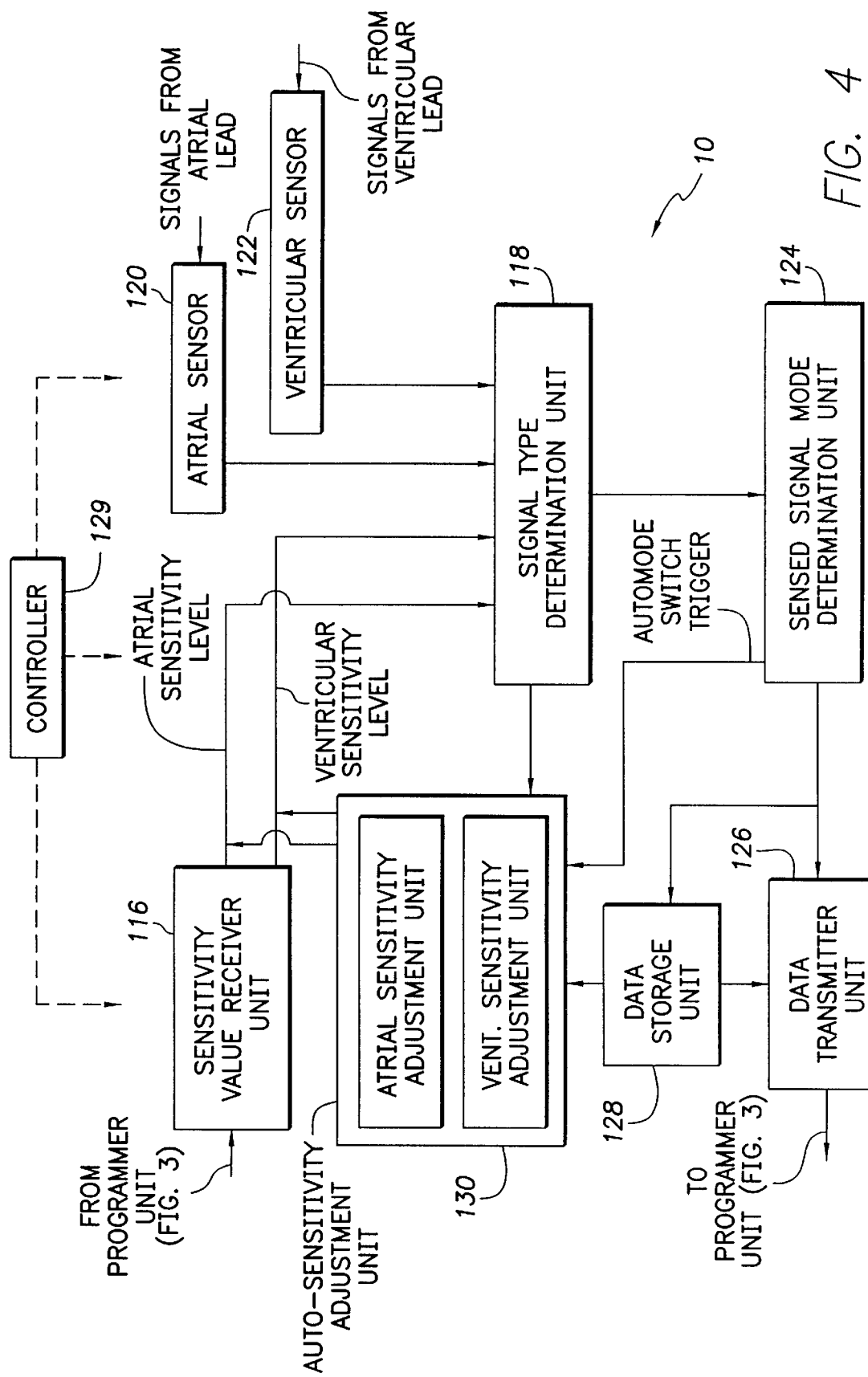
FIG. 4 is block diagram of pertinent components of an exemplary embodiment of the pacemaker of FIG. 1 for use in detecting P-waves and R-waves and transmitting data representative thereof to the external programmer of FIG. 3.

With reference to FIGS. 3 and 4, internal components of pacemaker 10 and external programmer 100 that are pertinent to the detection and processing of electrical heart activity signals by the pacemaker and to the generation of P-wave and R-wave histograms using the external programmer 100 will now be described. Components of programmer 100 are shown in FIG. 3. Components of pacemaker 10 are shown in FIG. 4. Referring first to FIG. 3, a controller 110 of the external programmer 100 controls graphic input/output device 104 to display the aforementioned menus from which the physician may select, among other options, to set atrial and ventricular sensitivity thresholds of the pacemaker 10 or to generate histograms based on P-wave and R-wave signals received from the pacemaker 10. Assuming that the physician has elected to set the atrial and ventricular sensitivity thresholds, a sensitivity selection unit 112 is controlled to present an appropriate threshold selection unit display screen to the physician via graphic input/output device 104 and to receive responsive selections. Absent any selection by the physician, sensitivity selection unit 112 sets the atrial and ventricular sensitivity threshold values to default values of, for example, 0.75 mv. A command transmitter unit 114 of telemetry head 106 transmits the selected sensitivity threshold values and/or other appropriate command signals to program the pacemaker 10 in the selected manner.

The atrial and ventricular sensitivity threshold values transmitted by the external programmer 100 are received by a sensitivity value receiver unit 116 and forwarded, under control of a controller 129, to a signal type determination unit 118. Signal type determination unit 118 also periodically or continuously receives electrical signals detected in the atrium of the heart via an atrial sensor 120 and electrical signals detected in the ventricle of the heart via a ventricular sensor 122.

Signal type determination unit 118 processes the detected atrial signals in accordance with the received atrial sensitivity threshold value to determine whether the detected atrial signals correspond to actual P-waves. To this end, the signal type determination unit 118 may employ conventional techniques to evaluate the shape and amplitude of the detected signals to determine whether the signals conform to expected shapes and amplitudes for actual P-waves. A part of this determination may be made by high pass filtering (typically with a 50 Hz cutoff) the detected signals to generate a signal having a filtered amplitude. If it is then determined that the detected signal has a filtered amplitude greater than a threshold sensitivity value, the detected signal is detected as a sensed P-wave.

In an alternative implementation, a frequency spectrum can also be determined for the filtered amplitude signal. The filtered amplitude of the detected signals is compared with the atrial sensitivity threshold and the frequency spectrum is compared with a range of predetermined acceptable frequency spectrums. If the detected signal has a filtered amplitude exceeding the threshold sensitivity value and has a frequency spectrum conforming to an expected P-wave, then the detected signal is identified as being a sensed P-wave signal and appropriate responsive actions are taken by other units of the pacemaker (not separately shown). As one example, if the pacemaker has previously been programmed to a DDI mode of operation, the detection of a sensed P-wave triggers an atrial refractory period in which further atrial signals are ignored. On the other hand, if the detected signal has a filtered amplitude falling significantly below the threshold sensitivity value or has a frequency spectrum substantially different from an expected P-wave, then the detected signal may be determined to not be a P-wave and is thereafter identified as a not-sensed signal and other appropriate action may be taken. For example, failure to detect a sensed P-wave within an expected time period may cause the pacemaker to trigger a pacing pulse.

In still other cases, if the detected signal has a filtered amplitude falling slightly below the threshold sensitivity value but has a frequency spectrum substantially conforming to an expected P-wave, then the detected signal may be identified as being a sensed signal. Also, if the detected signal has a filtered amplitude slightly exceeding the threshold sensitivity value but has a frequency spectrum substantially different from an expected P-wave, then the detected signal may be identified as being a not-sensed signal.

Signal type determination unit 118 also processes ventricular signals periodically or continuously provided by ventricular sensor 122 to determine whether the detected ventricular signals correspond to sensed or not-sensed R-wave signals. As with the atrial signals, a filtered amplitude and a frequency spectrum for the detected ventricular signals are determined. Then, the filtered amplitude is compared to the ventricular sensitivity threshold value and the frequency spectrum is compared against a range of acceptable frequency spectrums to determine whether the detected ventricular signal corresponds to an R-wave and, if so, the detected signal is identified as a sensed R-wave signal.

Details of techniques for detecting atrial and ventricular signals and for determining therefrom whether the respective signal corresponds to P-wave or an R-wave are described in U.S. Pat. No. 5,024,221 to Morgan entitled "Programmable Band-pass Amplifier for use with Implantable Medical Device" which is incorporated by reference herein.

Data signals representative of each detected atrial and ventricular signal are forwarded to a sensed signal mode determination unit 124. Each data signal includes the following parameters: the filtered amplitude of the corresponding atrial or ventricular signal; an indication of whether the corresponding atrial or ventricular signal is a sensed signal or a not-sensed signal; and the sensitivity threshold value used in making the sensed vs. not-sensed determination.

Sensed signal mode determination unit 124 determines whether the sensed signals were detected during either an alert period or a refractory period as well as its current operational mode, i.e., tracking (e.g., VDD, DDD) or non-tracking (e.g., DDI, VVI). Appropriate conventional techniques may be employed. For example, the sensed signal mode determination unit 124 may compare an atrial refractory period triggered by a previously sensed P-wave signal to determine whether a subsequently sensed P-wave or R-wave was detected within the refractory period. Similar techniques may be employed to determine whether sensed P-waves and R-waves were detected during an alert period. Also, the signal mode determination unit may track periods of time during which an alternate operational pacing mode is employed by the pacemaker to determine whether sensed P-waves and R-waves were detected. Specifically, in response to an automatic mode switching function (i.e., automode switch), the current pacing mode may switch from a tracking operational mode (e.g., VDD, DDD) to a non-tracking operational mode (e.g., DDI, VVI). Embodiments of the present invention preferably save this operational mode status in conjunction with the sensed, not-sensed, refractory and alert status.

Thereafter, sensed signal mode determination unit 124 forwards the data signals received from signal type determination unit 118 to a data transmitter unit 126 and to a data storage unit 128. (Sensed signal mode determination unit 124 also sends a signal indicative of the operational mode in response to an automode switch to an auto-sensitivity adjustment unit 130 which, as will be described below, automatically adjusts the atrial and ventricular sensitivity threshold values to alternative values.) As more and more atrial and ventricular signals are processed by signal type determination unit 118 and by sensed signal mode determination unit 124, more and more data signals are stored in the data storage unit 128, thereby developing a database of stored signals. For each data signal corresponding to a sensed P-wave or R-wave, the corresponding data signal received by the data transmitter 126 and stored by the data storage unit 128 includes, in addition to the aforementioned parameters, an indication of whether the respective sensed signal was detected within a refractory period or alert period and its current operational mode.

Data transmitter unit 126 transmits the data signals generated by sensed signal mode determination unit 124 to the external programmer 100 (FIG. 3). Depending upon programming, the data transmitter unit 126 either transmits the data signals substantially in real-time as the signals are received from the sensed signal mode determination unit 124 or transmits previously stored data signals maintained in the data storage unit 128. The latter may be appropriate if, for example, the data is recorded while the external programmer 100 is not in telemetry communication with the pacemaker 10. Whether transmitted in real-time or otherwise, data transmitter unit 126 operates to sequentially transmit a stream of signals corresponding to the atrial and ventricular electrical signals that had been detected by sensors 120 and 122 and processed by determination units 118 and 124.

Referring again to FIG. 3, the data signals transmitted by pacemaker 10, whether in real-time or otherwise, are sequentially received by a data receiver unit 132 of telemetry head 106 of the external programmer 100 and stored in a data storage unit 134. If the physician operating the external programmer 100 selects for display a P-wave histogram (using menus presented on graphic input/output device 104 under the control of controller 110), atrial signals previously stored in data storage unit 134 and any signals currently being received by the data receiver unit 132 are forwarded to a histogram generation unit 136 which generates a P-wave histogram therefrom for display on graphic input/output device 104 (or for print-out via printer 102). To this end, histogram generation unit 136 counts the total number of sensed and not-sensed atrial signals having filtered amplitude values within each of a set of predetermined filtered amplitude ranges, such as eight equal ranges from 0.0 mv to 3.00 mv. For each of the filtered amplitude ranges, the histogram generation unit then displays a histogram bar having a total height representative of the total number of sensed and not-sensed atrial signals within the range and having portions representative of the number of sensed counts and the number of not-sensed counts. The histogram generation unit 136 also displays the atrial sensitivity threshold value with which the atrial signals were sensed.

Figure 5:
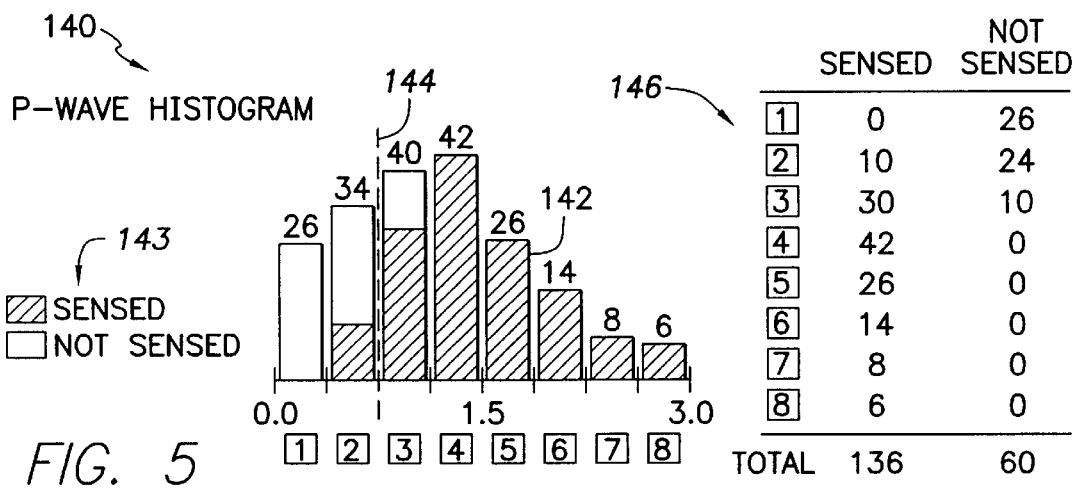
FIG. 5 is an exemplary P-wave histogram displayed by the external programmer of FIG. 2 wherein the histogram displays counts of sensed and not-sensed signals.

An exemplary P-wave histogram 140 is presented in FIG. 5. The exemplary histogram includes eight bars 142 each divided, where applicable, into sensed and not-sensed portions. A legend 143 identifies which portions of the histogram bars represent sensed signals and which portions represent not-sensed signals. A horizontal axis displays the range of filtered amplitudes. The atrial sensitivity threshold value is represented by a vertical line 144 displayed at the appropriate position along the x-axis. For the example of FIG. 5, the atrial sensitivity threshold value is 0.75 mv. A number is displayed over each bar identifying the total number of counts within the corresponding filtered amplitude range. A table 146 lists the total number of counts for both sensed and not-sensed signals.

As can be seen, about two thirds of the total number of atrial signals detected were identified as being sensed P-waves. Of those atrial signals having filtered amplitude values near the exemplary atrial sensitivity threshold value of 0.75 mv, about half were identified as being sensed signals and about half as not-sensed signals. Thus, some signals above the threshold value are identified as not-sensed and some signals below the threshold value are identified as sensed. Such can occur, as explained above, if there are either significant similarities or significant differences between the frequency spectrum of the detected signal and that of an expected P-wave.

Figure 6:
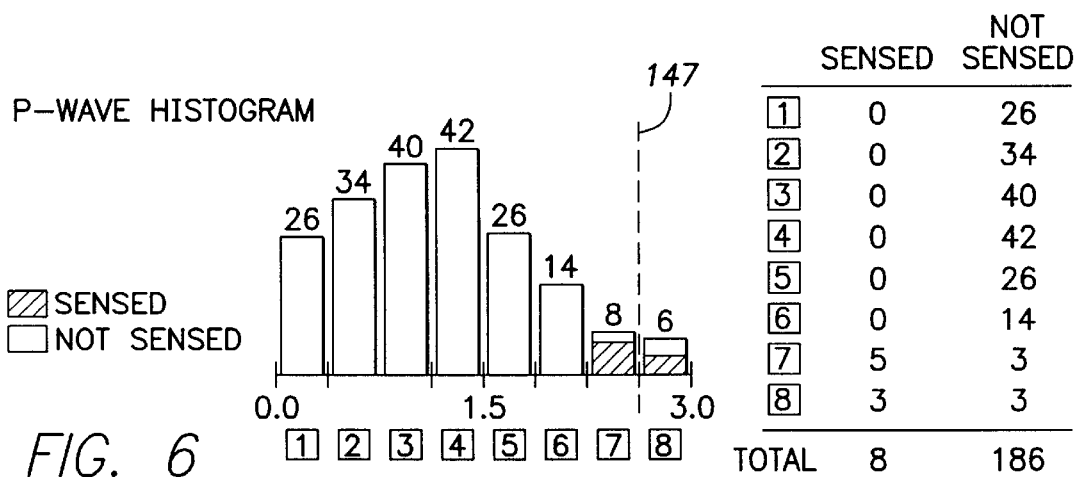
FIG. 6 is another exemplary P-wave histogram displayed by the external programmer of FIG. 2 showing P-wave data collected with an atrial sensitivity threshold value set too high.
Figure 7:
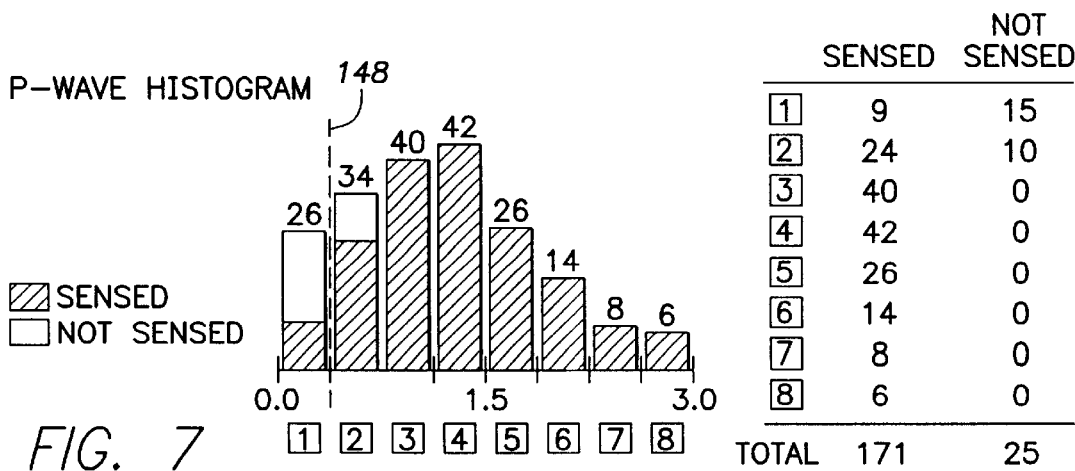
FIG. 7 is another exemplary P-wave histogram displayed by the external programmer of FIG. 2 showing P-wave data collected with an atrial sensitivity threshold value set too low.

With information of the type provided in FIG. 5, the physician operating the external programmer 100 can easily visually determine whether the atrial sensitivity threshold value is set to an appropriate value. Consider, for example, the exemplary P-wave histogram presented in FIG. 6 wherein relatively few of the total number of detected atrial signals are sensed and wherein the vast majority are not-sensed, indicative of an atrial sensitivity threshold value 147 set much too high. Consider, as another example, the exemplary P-wave histogram presented in FIG. 7 wherein substantially all of the total number of detected atrial signals are sensed and wherein virtually none are not-sensed, indicative of an atrial sensitivity threshold value 148 set much too low.

Figure 8A:
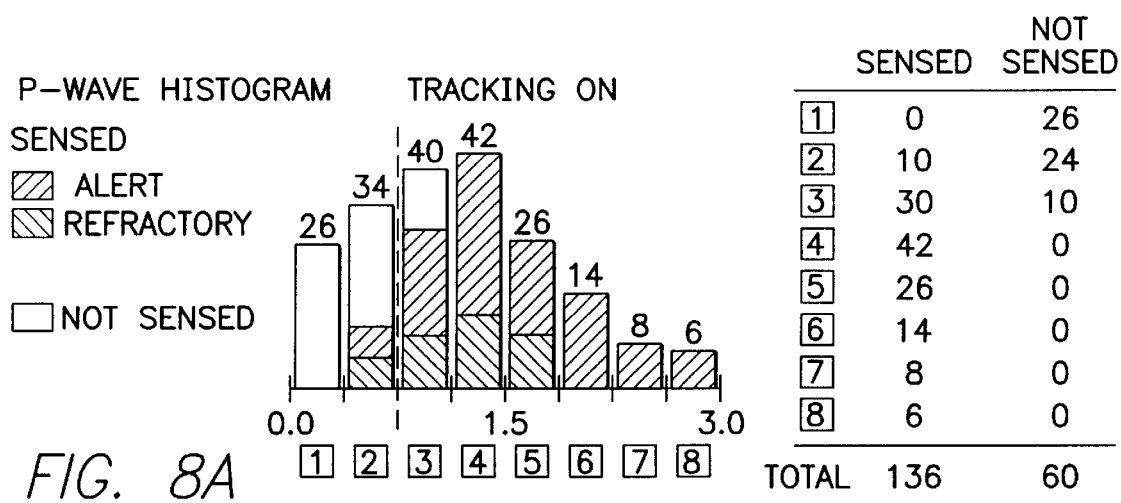
FIG. 8A is an alternative exemplary P-wave histogram displayed by the external programmer of FIG. 2 for a tracking (e.g., VDD, DDD) mode of operation wherein information regarding data collected during a refractory period and an alert period is additionally represented.
Figure 9A:
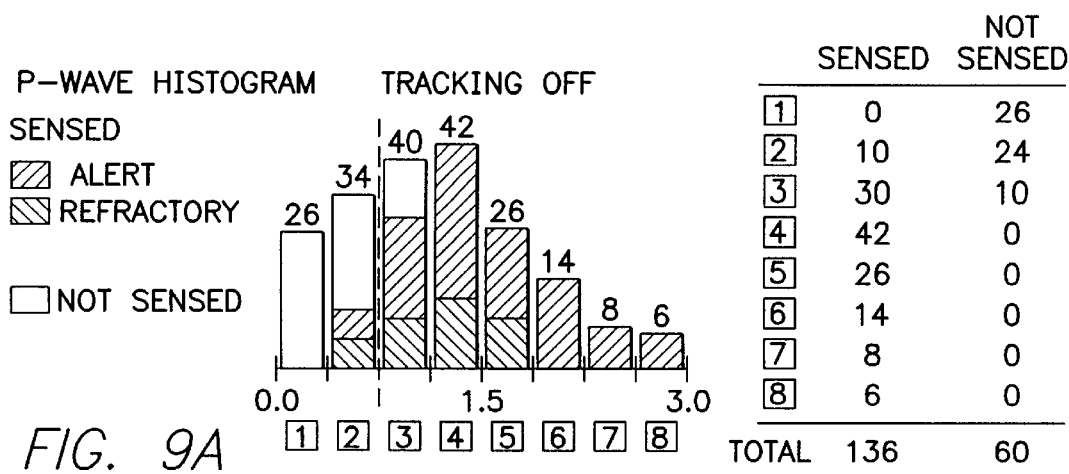
FIG. 9A is an alternative exemplary P-wave histogram displayed by the external programmer of FIG. 2 for a non-tracking (e.g., DDI, VVI) mode of operation wherein information regarding data collected during a refractory period and an alert period is additionally represented.

Alternatively, histograms may be generated which additionally distinguish among the various sensed signals to identify which portions, if any, were detected during refractory periods or alert periods (preferably in reference to its current operational mode) to thereby give the physician even more information for use in determining whether the atrial sensitivity threshold value is set properly. An exemplary histogram display which additionally distinguishes among portions detected during refractory periods or alert periods is provided in FIGS. 8A and 9A. In this example, FIG. 8A shows an exemplary histogram display when the current operational mode is a tracking mode (e.g., VDD, DDD) and FIG. 9A shows an exemplary histogram display when the current operational mode is a non-tracking mode (e.g., DDI, VVI).

Figure 8B:
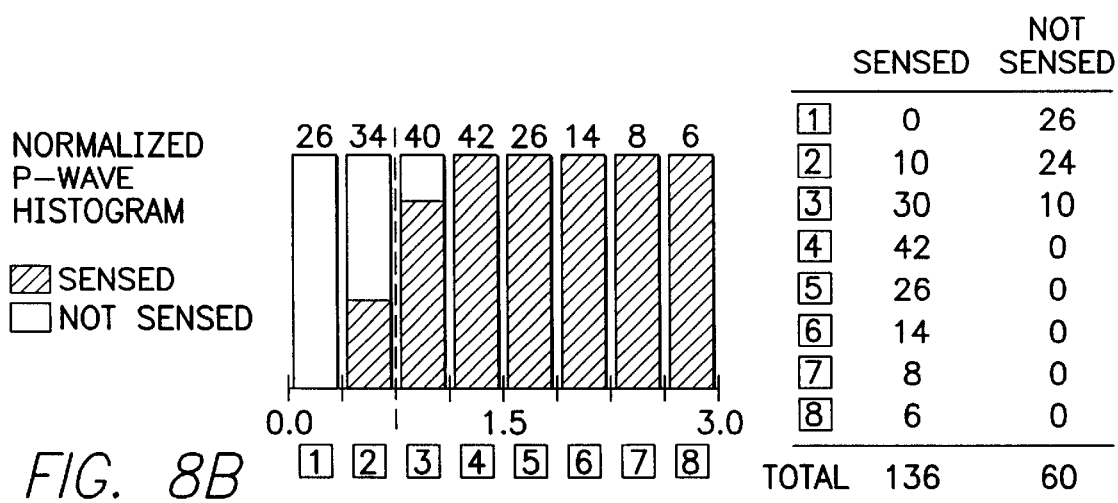
FIG. 8B is another alternative view of the exemplary P-wave histogram of FIG. 8A displayed by the external programmer of FIG. 2 wherein the data is normalized.
Figure 9B:
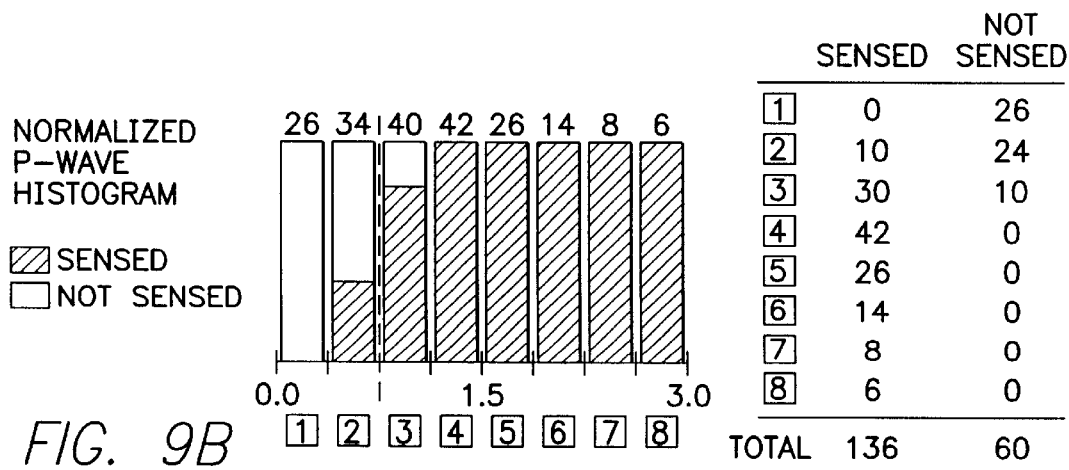
FIG. 9B is another alternative view of the exemplary P-wave histogram of FIG. 9A displayed by the external programmer of FIG. 2 wherein the data is normalized.
Figure 10:
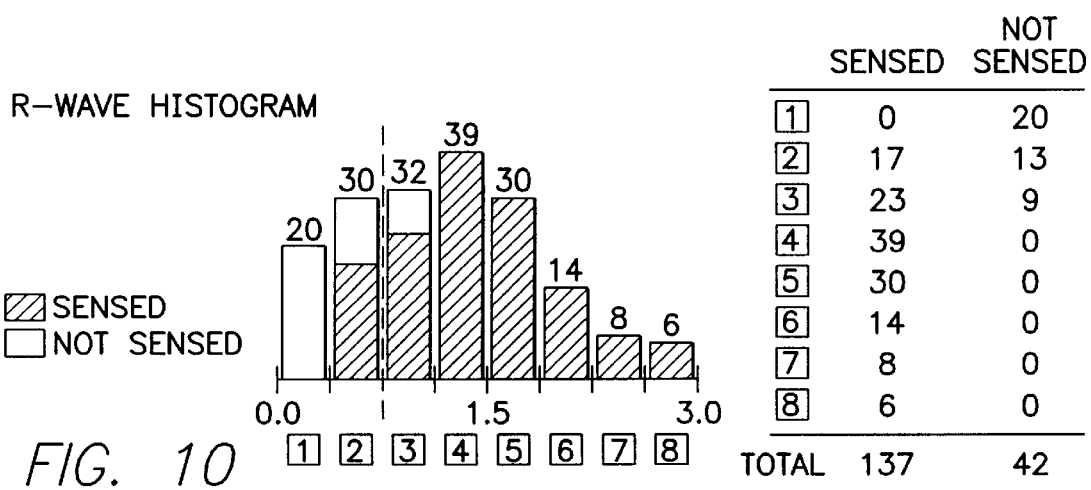
FIG. 10 is an exemplary R-wave histogram displayed by the external programmer of FIG. 2 wherein the histogram displays counts of sensed and not-sensed signals.
Figure 11:
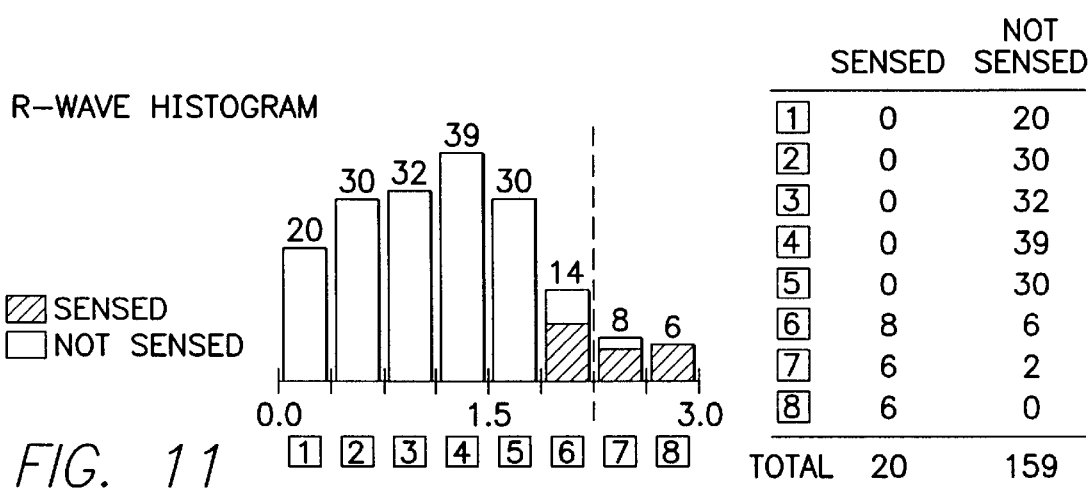
FIG. 11 is another exemplary R-wave histogram displayed by the external programmer of FIG. 2 showing R-wave data collected with a ventricular sensitivity threshold value set too high.
Figure 12:
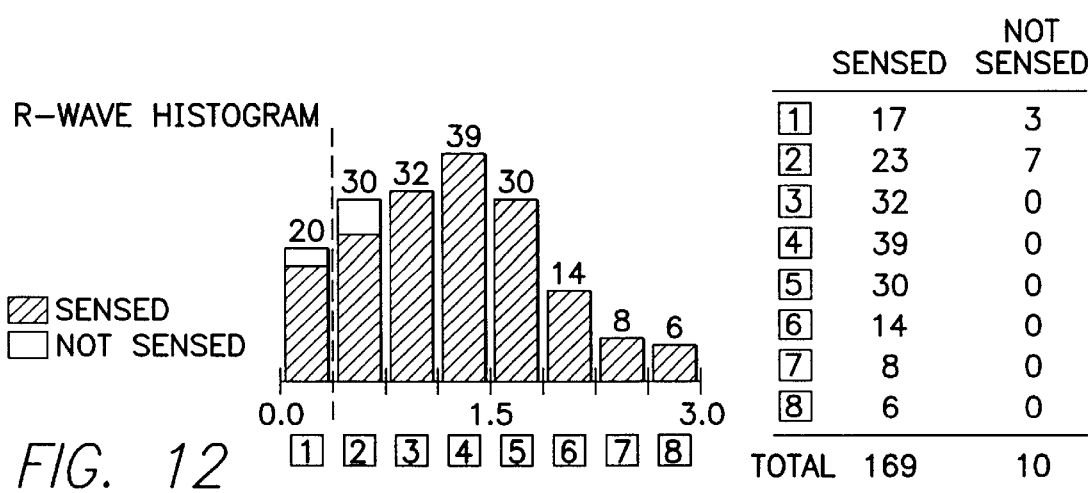
FIG. 12 is another exemplary R-wave histogram displayed by the external programmer of FIG. 2 showing R-wave data collected with a ventricular sensitivity threshold value set too low.
Figure 13:
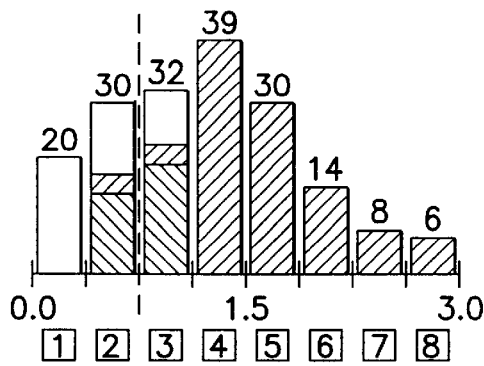
FIG. 13 is an alternative exemplary R-wave histogram displayed by the external programmer of FIG. 2 wherein information regarding data collected during a refractory period and an alert period is additionally represented.
Figure 14:
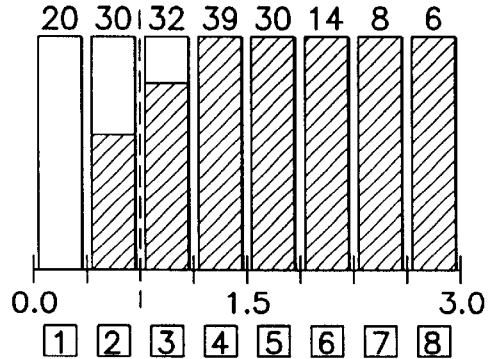
FIG. 14 is alternative view of the exemplary R-wave histogram of FIG. 13 displayed by the external programmer of FIG. 2 wherein the data is normalized.

Still other displays may be generated wherein the histogram data is presented in a normalized form to allow the physician to more easily see the relative proportions of counts that are sensed or not-sensed. An exemplary normalized display is presented in FIG. 8B (tracking mode) and FIG. 9B (non-tracking mode). Although not shown, still other normalized histograms may be generated additionally distinguishing among portions detected during refractory periods or, alert periods.

Exemplary R-wave histograms are presented in FIGS. 10–14. The histograms of FIGS. 10–14 are similar to the P-wave histograms of FIGS. 5–9 and will not be further described.

Thus, a few exemplary displays of histogram data have been specifically illustrated. It should be noted that a wide variety of other types of histogram displays may alternatively be generated in accordance with the principles of the invention.

Also, although not shown, the various P-wave and R-wave histograms may present additional textual information such as, for example, text identifying when detection of the histogram signals was initiated. As another example, the external programmer 100 may allow the physician to freeze the histogram while ignoring any further data received by the external programmer 100. In such a case, text may be presented identifying whether the histogram display is frozen and, if so, when the display was frozen. Moreover, the external programmer 100 may allow the physician to selectively clear the data storage unit 134 to allow for generation of histograms based only on more recently received data. If such is the case, text may be displayed identifying when the data storage unit 134 was last cleared. In still other implementations, the histogram display may additionally include a running real-time display of an IEGM detected by the pacemaker 10 such that the physician can observe the IEGM while simultaneously viewing the P-wave or R-wave histograms.

What has been described thus far is the generation of histograms representative of P-wave and R-wave signals from which the physician can visually determine whether atrial and ventricular sensitivity threshold values are set properly. The following describes techniques for automatically determining more optimal threshold values.

Referring again to FIG. 3, a sensitivity recommendation unit 150 is provided to assist the physician in selecting a new atrial or ventricular sensitivity threshold value, if such is warranted. Under the control of the physician via appropriate menus presented on graphic input/output device 104, the sensitivity recommendation unit 150 determines more optimal sensitivity threshold values by analyzing the atrial and ventricular histogram data stored in data storage unit 134 and presented in the current histogram display. To this end, the sensitivity recommendation unit 150 compares the relative numbers of counts within the various aforementioned categories (i.e., sensed vs. not-sensed or refractory vs. alert, etc.) and, by applying pre-stored optimization rules, selects new sensitivity threshold values. Depending upon specific programming, a wide variety of appropriate optimization rules consistent with generally accepted medical judgment may be incorporated. In one example, the sensitivity recommendation unit 150 determines the filtered amplitude having the largest number of counts and preferably sets the sensitivity threshold value to approximately half that amount. The sensitivity recommendation unit 150 also sets the sensitivity threshold value such that approximately equal numbers of the counts having filtered amplitude values near the new sensitivity threshold values will be sensed and equal numbers will be not-sensed. In the example, the sensitivity recommendation unit 150 may be further programmed to adjust the sensitivity to reduce the numbers of counts detected during refractory periods or alert periods. As can be appreciated, a wide variety of optimization rules may be programmed into the sensitivity recommendation unit 150 to achieve a more optimal recommendation. Fuzzy logic, or other appropriate logic techniques, may be employed.

Once the sensitivity recommendation unit 150 has determined more optimal values for the atrial and ventricular sensitivity threshold values, the more optimal values presented by sensitivity selection unit 112 are presented to the physician via an appropriate display (not shown) and the physician then has the choice of: accepting the recommended values, setting the sensitivity values to other values, or leaving the sensitivity values at previous values. If the physician elects to change the sensitivity threshold values, the new values are transmitted to the pacemaker 10 via command transmitter unit 114. Preferably, the respective data storage units 134, 128 in the external programmer 100 and the pacemaker 10 are both cleared upon selection of new sensitivity threshold values to ensure that histogram data previously recorded at different sensitivity threshold values is not merged with histogram data subsequently recorded at the new sensitivity threshold values.

Referring again to FIG. 4, atrial and ventricular sensitivity adjustment capability is additionally provided directly within the pacemaker 10 by an auto-sensitivity adjustment unit 130. If programmed to do so by signals received from the external programmer 100, auto-sensitivity adjustment unit 130 periodically retrieves atrial and ventricular data from data storage unit 128, analyzes the data, and determines more optimal atrial and ventricular sensitivity threshold values therefrom. To this end, auto-sensitivity adjustment unit 130 may use the same or similar optimization rules as employed by sensitivity recommendation unit 150 of the external programmer 100 (FIG. 3). Alternatively, auto-sensitivity adjustment unit 130 is programmed to only adjust the sensitivities upon detection of an automode switching event occurring upon the onset of an atrial tachycardia within the heart tissue (as determined by pacemaker components not separately shown). In yet another alternative embodiment, auto-sensitivity adjustment unit 130 is programmed to adjust the sensitivity values upon detection of an automode switching event, i.e., switching from a tracking (e.g., VDD, DDD) to a non-tracking (e.g., DDI, VVI) operational mode, occurring to treat the onset of an atrial tachycardia but only changes the thresholds to predetermined alternate values. In other words, in this alternative embodiment, the auto-sensitivity adjustment unit 130 does not analyze the stored atrial and ventricular data to determine more optimal sensitivity threshold values, but merely sets the sensitivity threshold values to predetermined alternate values. In any case, whenever an adjustment to the sensitivity values is made, data storage unit 128 is preferably cleared. Also, once any atrial and ventricular data signals detected using the new sensitivity threshold values are sent to the external programmer 100, the data storage unit 134 of the external programmer 100 is also preferably cleared. This function may be triggered within the external programmer 100 by, for example, comparing the sensitivity threshold values of previously stored data with the sensitivity values of newly received data and clearing the data storage unit 134 whenever a discrepancy is detected.

What has been described are systems for detecting and processing atrial and ventricular signals using a pacemaker, for generating and displaying histograms based upon the atrial and ventricular signals using an external programmer, and for determining more optimal atrial and ventricular threshold sensitivity values. The various functional components of the exemplary pacemaker and external programmer system may be implemented using any appropriate technology including, for example, microprocessors running software programs or application specific integrated circuits (ASICs) executing hard-wired logic operations. Although described with respect to a pacemaker used in conjunction with an external programmer, aspects of the invention are applicable to other systems, such as systems employing other implantable medical devices or systems employing other types of external interfaces for use with the implantable device. The exemplary embodiments of the invention described herein are merely illustrative of the invention. Consequently, the scope of the invention should not be limited to the foregoing description but is to be defined by the appended claims.

What is claimed is:

1. A method for processing information using an implantable medical device and an external display device wherein the implantable medical device is connected to heart tissue and is capable of sensing electrical activity within the heart tissue, the method comprising the steps of:

detecting a plurality of signals representative of electrical depolarization activity within the heart tissue connected to the implantable medical device;

determining for each respective detected signal whether the signal corresponds to a predetermined type of heart tissue depolarization and the degree of depolarization;

transmitting to the external display device a signal representative of the degree of depolarization for each respective detected signal as well as a signal indicative of whether each respective detected signal is of the predetermined type of heart tissue depolarization;

receiving the transmitted signals at the external display device;

processing the received signals at the external display device to generate a histogram representative of the plurality of detected signals as a function of the degree of depolarization of the signals and further representative of whether the signals were determined to correspond to the predetermined type of heart tissue depolarization; and graphically displaying the histogram at the external display device.

2. The method of claim 1, wherein the predetermined type of heart tissue depolarization is a P-wave.

3. The method of claim 1, wherein the predetermined type of heart tissue depolarization is an R-wave.

4. The method of claim 1, wherein the step of graphically displaying the histogram is performed to identify signals corresponding to the predetermined type of heart tissue depolarization in the histogram as sensed signals and to identify signals not corresponding to the predetermined type of heart tissue depolarization in the histogram as not-sensed signals.

5. The method of claim 4, further including the step of determining the portion of the sensed signals that were detected during either an alert period or a refractory period.

6. The method of claim 5, wherein the step of determining the portion of the sensed signals that were detected during either an alert period or a refractory period is determined in conjunction with the current operational mode of the implantable medical device.

7. The method of claim 5, wherein the step of graphically displaying the histogram includes the step of identifying the respective portions of the sensed signals found to have been detected during the alert period and the refractory period.

8. The method of claim 5, wherein the step of graphically displaying the histogram additionally includes separately displaying histograms according to the current operational mode of the implantable medical device.

9. The method of claim 1, wherein at least a portion of the step of determining whether each signal corresponds to a predetermined type of heart tissue depolarization is performed by filtering each signal to determine a filtered amplitude of each signal and by comparing the filtered amplitude of each signal with a predetermined sensitivity threshold value.

10. The method of claim 9, wherein the step of graphically displaying the histogram includes the step of displaying the predetermined sensitivity threshold value.

11. The method of claim 9, wherein the step of graphically displaying the histogram includes the step of displaying a range of filtered amplitude values corresponding to predetermined degrees of depolarization.

12. The method of claim 9, wherein signals that are determined to correspond to the predetermined type of heart tissue depolarization are identified as sensed signals and signals that are determined to not correspond to the predetermined type of heart tissue depolarization are identified as not-sensed signals and wherein the method includes the further step of adjusting the predetermined sensitivity threshold value based upon a comparison of a ratio of the number of sensed and not-sensed signals received.

13. The method of claim 12, further including the steps of detecting an automode switching event occurring upon the onset of an atrial tachycardia within the heart tissue and wherein the step of adjusting the predetermined sensitivity threshold value is triggered upon detection of the automode switching event.

14. A system for processing information within an implantable medical device and an external display device wherein the implantable medical device is connected to heart tissue and is capable of sensing electrical activity within the heart tissue, the system comprising:

means within the implantable medical device for detecting a plurality of signals representative of electrical depolarization activity within the heart tissue connected to the implantable medical device;

means for determining the degree of polarization for each respective detected signal and whether the signal corresponds to a predetermined type of heart tissue depolarization; and means within the external display device for processing the signals to graphically display a histogram representative of the plurality of detected signals as a function of the degree of depolarization of the signals and further representative of whether the signals were determined to correspond to the predetermined type of heart tissue depolarization.

15. The system of claim 14, wherein the predetermined type of heart tissue depolarization is a P-wave.

16. The system of claim 14, wherein the predetermined type of heart tissue depolarization is an R-wave.

17. The system of claim 14, wherein the means for processing the signal to graphically display a histogram additionally identifies signals corresponding to the predetermined type of heart tissue depolarization in the histogram as sensed signals and identifies signals not corresponding to the predetermined type of heart tissue depolarization in the histogram as not-sensed signals.

18. The system of claim 17, further including means for determining the portion of the sensed signals that were detected during either an alert period or a refractory period.

19. The system of claim 18, wherein the means for determining the portion of the sensed signals that were detected during either an alert period or a refractory period is determined in conjunction with the current operational mode of the implantable medical device.

20. The system of claim 18, wherein the means for processing the signals to graphically display a histogram additionally operates to identify in the histogram the respective portions of the sensed signals found to have been detected during the alert period or the refractory period.

21. The method of claim 18, wherein the means for processing the signals to graphically display a histogram additionally includes separately displaying histograms according to the current operational mode of the implantable medical device.

22. The system of claim 14, wherein the means for determining whether each signal corresponds to a predetermined type of heart tissue depolarization operates, in part, to filter each signal to determine a filtered amplitude of each signal and to compare the filtered amplitude of each signal with a predetermined sensitivity threshold value.

23. The system of claim 22, wherein the means for processing signals to graphically display the histogram additionally operates to display the predetermined sensitivity threshold value.

24. The system of claim 22, wherein the means for processing signals to graphically display the histogram additionally operates to display a range of filtered amplitude values corresponding to predetermined degrees of depolarization.

25. The system of claim 22, wherein the means for determining whether the signal corresponds to a predetermined type of heart tissue depolarization operates to identify signals corresponding to the predetermined type of heart tissue depolarization as sensed signals and to identify signals not corresponding to the predetermined type of heart tissue depolarization as not-sensed signals and wherein the system includes means for adjusting the predetermined sensitivity threshold value based upon a comparison of a ratio of the number of sensed and not-sensed signals received.

26. The system of claim 25, further including means for detecting an automode switching event occurring upon the onset of an atrial tachycardia within the heart tissue and wherein operation of the means for adjusting the predetermined sensitivity threshold value is triggered upon detection of the automode switching event.

27. A system for processing information within an implantable medical device and an external display device wherein the implantable medical device is connected to heart tissue and is capable of sensing electrical activity within the heart tissue, the system comprising:
  a detector within the implantable medical device for detecting a plurality of signals representative of electrical depolarization activity within the heart tissue connected to the implantable medical device;
  a signal type determination unit for determining for each detected signal whether the signal corresponds to a predetermined type of heart tissue depolarization;
  a histogram generation unit within the external display device for processing the signals to generate a histogram representative of the plurality of signals as a function of the degree of depolarization of the signals and further representative of whether the signals were determined to correspond to the predetermined type of heart tissue depolarization; and
  a graphic display unit within the external display device for graphically displaying the histogram.

28. The system of claim 27, wherein the predetermined type of heart tissue depolarization is a P-wave.

29. The system of claim 27, wherein the predetermined type of heart tissue depolarization is an R-wave.

30. The system of claim 27, wherein the histogram generation unit identifies signals corresponding to the predetermined type of heart tissue depolarization in the histogram as sensed signals and identifies signals not corresponding to the predetermined type of heart tissue depolarization in the histogram as not-sensed signals.

31. The system of claim 30, further including a sensed signal classification unit for determining the portion of the sensed signals that were detected during either an alert period or a refractory period.

32. The method of claim 31, wherein the sensed signal classification unit determines the portion of the sensed signals that were detected during either an alert period or a refractory period in conjunction with the current operational mode of the implantable medical device.

33. The system of claim 31, wherein the histogram generation unit operates to identify in the histogram the respective portions of the sensed signals found to have been detected during the alert period or the refractory period.

34. The system of claim 31, wherein the histogram generation unit generates separate histograms to display the sensed signal detected during the alert period or the refractory period according to the current operational mode of the implantable medical device.

35. The system of claim 27, wherein at least a portion of the signal type determination unit operates to filter each signal to determine a filtered amplitude of each signal and to compare the filtered amplitude of each signal with a predetermined sensitivity threshold value.

36. The system of claim 35, wherein the graphic display unit is controlled to also display the predetermined sensitivity threshold value.

37. The system of claim 35, wherein the graphic display unit is also controlled to display a range of filtered amplitude values corresponding to predetermined degrees of depolarization.

38. The system of claim 35, wherein the signal type determination unit operates to identify signals corresponding to the predetermined type of heart tissue depolarization as sensed signals and to identify signals not corresponding to the predetermined type of heart tissue depolarization as not-sensed signals and wherein the system includes a sensitivity adjustment unit for adjusting the predetermined sensitivity threshold value based upon a comparison of a ratio of the number of sensed and not-sensed signals identified.

39. The system of claim 38, further including an automode switching event detection unit for detecting an automode switching event occurring upon the onset of an atrial tachycardia within the heart tissue and wherein operation of the sensitivity adjustment unit is triggered upon detection of an automode switching event.

40. A system for processing information within an implantable medical device wherein the implantable medical device is connected to heart tissue and is capable of sensing electrical activity within the heart tissue, the system comprising:

a detector within the implantable medical device for detecting a plurality of signals representative of electrical depolarization activity within the heart tissue connected to the implantable medical device;

a signal type determination unit for determining for each detected signal whether the signal corresponds to a predetermined type of heart tissue depolarization;

a histogram generation unit for processing the signals to generate histogram data representative of the plurality of signals as a function of the degree of depolarization of the signals and further representative of whether the signals were determined to correspond to the predetermined type of heart tissue depolarization; and a sensitivity adjustment unit for determining a sensitivity threshold level for determining the type of heart tissue depolarization in response to the generated histogram data.

41. The system of claim 40, wherein the predetermined type of heart tissue depolarization is a P-wave.

42. The system of claim 40, wherein the predetermined type of heart tissue depolarization is an R-wave.

43. The system of claim 40, wherein the histogram generation unit identifies signals corresponding to the predetermined type of heart tissue depolarization in the histogram as sensed signals and identifies signals not corresponding to the predetermined type of heart tissue depolarization in the histogram as not-sensed signals.

44. The system of claim 43, further including a sensed signal classification unit for determining the portion of the sensed signals that were detected during either an alert period or a refractory period.

45. The system of claim 44, wherein the sensed signal classification unit additional determines the portion of the sensed signal detected during either an alert period or a refractory period in conjunction with the current operational mode of the implantable medical device.

46. The system of claim 44, wherein the histogram generation unit operates to identify in the histogram data the respective portions of the sensed signals found to have been detected during the alert period or the refractory period.

47. The system of claim 44, wherein the histogram generation unit separately displays histograms according the current operational mode of the implantable medical device to identify in the histogram data the respective portions of the sensed signals found to have been detected during the alert period or the refractory period.

48. The system of claim 40, wherein at least a portion of the signal type determination unit operates to filter each signal to determine a filtered amplitude of each signal and to compare the filtered amplitude of each detected signal with a determined sensitivity threshold value.

49. The system of claim 48, wherein the signal type determination unit operates to identify signals corresponding to the predetermined type of heart tissue depolarization as sensed signals and to identify signals not corresponding to the predetermined type of heart tissue depolarization as not-sensed signals and wherein the sensitivity adjustment unit adjusts the determined sensitivity threshold value based upon a comparison of a ratio of the number of sensed and not-sensed signals identified.

50. The system of claim 40, further including an automode switching event detection unit for detecting an automode switching event occurring upon the onset of an atrial tachycardia within the heart tissue and wherein operation of the sensitivity adjustment unit is triggered upon detection of an automode switching event.

* * * * *